US012045916B2

(12) United States Patent
Stayman et al.

(10) Patent No.: US 12,045,916 B2
(45) Date of Patent: Jul. 23, 2024

(54) STOCHASTIC BACKPROJECTION FOR 3D IMAGE RECONSTRUCTION

(71) Applicant: THE JOHNS HOPKINS UNIVERSITY, Baltimore, MD (US)

(72) Inventors: Joseph Webster Stayman, Baltimore, MD (US); Alejandro Sisniega, Baltimore, MD (US); Jeffrey H. Siewerdsen, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 771 days.

(21) Appl. No.: 17/110,743

(22) Filed: Dec. 3, 2020

(65) Prior Publication Data
US 2021/0174561 A1 Jun. 10, 2021

Related U.S. Application Data

(60) Provisional application No. 62/943,582, filed on Dec. 4, 2019.

(51) Int. Cl.
G06T 11/00 (2006.01)
A61B 6/03 (2006.01)
(Continued)

(52) U.S. Cl.
CPC ............ G06T 11/008 (2013.01); A61B 6/032 (2013.01); A61B 6/4233 (2013.01); A61B 6/466 (2013.01);
(Continued)

(58) Field of Classification Search
CPC .... G06T 11/003; G06T 11/006; G06T 11/008; G06T 15/08; G06T 2207/10081;
(Continued)

(56) References Cited

U.S. PATENT DOCUMENTS

2010/0150421 A1* 6/2010 Nakanishi ............. G06T 11/006
378/4
2014/0218362 A1* 8/2014 Gindele ............... A61B 6/5205
345/424
2014/0270443 A1* 9/2014 Vija ..................... A61B 6/5258
382/131

OTHER PUBLICATIONS

Jakab et al., "High quality cone-beam CT reconstruction on the GPU", Jan. 2011. Képfeldolgozók és Alakfelismerők Társasága, In: 8th KEPAF Conference, <http://www.inf.u-szeged.hu/projectdirs/kepaf2011/proceedings.php>, p. 70-82. (Year: 2011).*

(Continued)

Primary Examiner — Vincent Rudolph
Assistant Examiner — Timothy Choi
(74) Attorney, Agent, or Firm — MH2 TECHNOLOGY LAW GROUP LLP

(57) ABSTRACT

Techniques for computed tomography (CT) image reconstruction are presented. The techniques can include acquiring, by a detector grid of a computed tomography system, detector signals for a location within an object of interest representing a voxel, where each detector signal of a plurality of the detector signals is obtained from an x-ray passing through the location at a different viewing angle; reconstructing a three-dimensional representation of at least the object of interest, the three-dimensional representation comprising the voxel, where the reconstructing comprises computationally perturbing a location of each detector signal of the plurality of detector signals within the detector grid, where the computationally perturbing corresponds to randomly perturbing a location of the x-ray within the voxel; and outputting the three-dimensional representation.

24 Claims, 13 Drawing Sheets

(51) Int. Cl.
   *A61B 6/42* (2024.01)
   *A61B 6/46* (2024.01)
   *G06T 15/08* (2011.01)

(52) U.S. Cl.
   CPC .......... *G06T 11/003* (2013.01); *G06T 11/006* (2013.01); *G06T 15/08* (2013.01); *G06T 2207/10081* (2013.01); *G06T 2210/41* (2013.01); *G06T 2211/421* (2013.01); *G06T 2211/424* (2013.01); *G06T 2211/432* (2013.01)

(58) Field of Classification Search
   CPC ....... G06T 2207/20076; G06T 2210/41; G06T 2211/42142; G06T 2211/4432; A61B 6/42; A61B 6/4208; A61B 6/4233; A61B 6/461; A61B 6/466; A61B 6/032; A61B 6/5205; A61B 6/5258
   See application file for complete search history.

(56) References Cited

OTHER PUBLICATIONS

Dang et al., "Multi-resolution statistical image reconstruction for mitigation of truncation effects: application to conebeam CT of the head", Jan. 2017, Institute of Physics and Engineering in Medicine, Physics in Medicine and Biology, 62(2), p. 539-559. (Year: 2017).*

Karimi et al., "A hybrid stochastic-deterministic gradient descent algorithm for image reconstruction in cone-beam computed tomography", Feb. 2016, Biomedical Physics & Engineering Express, vol. 2, No. 1, p. 1-17. (Year: 2016).*

Wang et al., "Accelerated statistical reconstruction for C-arm cone-beam CT using Nesterov's method", May 2015, American Association of Physicists in Medicine, Medical Physics, 42(5), p. 2699-2708. (Year: 2015).*

Jones et al., "Efficient Generation of Poisson-Disk Sampling Patterns", Apr. 2006, Taylor & Francis, Journal of Graphics GPU and Game Tools, p. 1-10. (Year: 2006).*

Andreyev et al. "Fast image reconstruction for Compton camera using stochastic origin ensemble approach", Jan. 2011, Am. Assoc. Phys. Med., Medical Physics, vol. 38, iss. 1, p. 429-438. (Year: 2011).*

Sitek et al., "Representation of photon limited data in emission tomography using origin ensembles", May 2008, IOP Publishing, Physics in Medicine & Biology, vol. 53, No. 12, p. 3201-3216. (Year: 2008).*

Boo et al., "Stochastic Optimization Approaches to Image Reconstruction in Electrical Impedance Tomography", Mar. 2010, Springer-Verlag, Int. Conf. on Computational Science and Its Applications (ICCSA 2010), part II, LNCS 6017, p. 99-109. (Year: 2010).*

Cao et al., "Multiresolution iterative reconstruction in high-resolution extremity cone-beam CT", Phys. Med. Biol., (2016), vol. 61, No. 20, pp. 7263-7281.

Wang et al., "Soft-tissue imaging with C-arm cone-beam CT using statistical reconstruction", Phys. Med. Biol., (2014), vol. 59, No. 4, pp. 1005-1026.

Marin et al., "Low-tube-voltage, high-tube-current multidetector abdominal CT: improved image quality and decreased radiation dose with adaptive statistical iterative reconstruction algorithm—initial clinical experience", Radiology, (2010), vol. 254, No. 1, pp. 145-153.

Yamada et al., "Dose reduction in chest CT: Comparison of the adaptive iterative dose reduction 3D, adaptive iterative dose reduction, and filtered back projection reconstruction techniques", European Journal of Radiology, (2012), vol. 81, No. 12, pp. 4185-4195.

Mieville et al., "Iterative reconstruction methods in two different MDCT scanners: Physical metrics and 4-alternative forced-choice detectability experiments—A phantom approach", Phys. Medica, (2013), vol. 29, No. 1, pp. 99-110.

Sauer et al., "Local update strategy for iterative reconstruction from projections", IEEE Trans. Signal Process., (1993), vol. 41, No. 2, pp. 534-549.

Erdogan et al., "Ordered subsets algorithms for transmission tomography", Phys. Med. Biol., (1999), vol. 44, No. 11, pp. 2835-2851.

Wang et al., "Accelerated statistical reconstruction for C-arm cone-beam CT using Nesterov's method", Med. Phys., (2015), vol. 42, No. 5, pp. 2699-2708.

Dang et al., "Multi-resolution statistical image reconstruction for mitigation of truncation effects: Application to cone-beam CT of the head", Phys. Med. Biol., (2017), vol. 62, No. 2, pp. 539-559.

* cited by examiner

STOCHASTIC BACKPROJECTION FOR 3D IMAGE RECONSTRUCTION

RELATED APPLICATION

This application claims priority to, and the benefit of, U.S. Provisional Patent Application No. 62/943,582, entitled, "Stochastic Backprojection For 3D Image Reconstruction," and filed Dec. 4, 2019, which is hereby incorporated by reference in its entirety.

FIELD

This disclosure relates generally to image reconstruction for medical imaging.

BACKGROUND

Medical imaging includes Computed Tomography (CT), Magnetic Resonance Imaging (MRI), X-rays, sonograms, and other techniques. CT includes both Transmission Computed Tomography (TCT) such as x-ray helical or axial multi-detector computed tomography (MDCT) and cone-beam computed tomography (CBCT), and Emission Computed Tomography (ECT) such as Positron Emission Tomography (PET) and Single-Photon Emission Computed Tomography (SPECT). Some medical imaging techniques produce three-dimensional images of objects of interest, such as patient injury sites. To generate three-dimensional images, large amounts of data received by one or more sensors of a medical imaging device is synthesized using a process known as image "reconstruction". Image reconstruction is computationally intensive and may lead to image artifacts if not performed carefully.

SUMMARY

According to various embodiments, a method of computed tomography (CT) image reconstruction is presented. The method includes acquiring, by a detector grid of a computed tomography system, detector signals for a location within an object of interest representing a voxel, where each detector signal of a plurality of the detector signals is obtained from an x-ray passing through the location at a different viewing angle; reconstructing a three-dimensional representation of at least the object of interest, the three-dimensional representation including the voxel, where the reconstructing includes computationally perturbing a location of each detector signal of the plurality of detector signals within the detector grid, where the computationally perturbing corresponds to randomly perturbing a location of the x-ray within the voxel; and outputting the three-dimensional representation.

Various optional features of the above embodiments include the following. The reconstructing may include reconstructing according to a three-dimensional grid including the voxel and a plurality of other voxels, where each of the voxel and the plurality of other voxels has a same size. The reconstructing may include reconstructing according to a three-dimensional grid including the voxel and a plurality of other voxels, where the voxel and the plurality of other voxels include voxels of at least two different sizes. The voxel and the plurality of other voxels may consist of coarse voxels and fine voxels, where the object of interest is contained within the fine voxels. The acquiring, by the detector grid of the computed tomography system, the plurality of detector signals for the location within the object of interest may consist of acquiring less than 100 detector signals. The outputting may include displaying on a computer monitor. The randomly perturbing the location of the X-ray within the voxel may include relocating to a distance from a center of the voxel, where the distance is obtained from a statistical random distribution. The randomly perturbing the location of the X-ray within the voxel may include selecting a random direction from a center of the voxel. The method may further include modifying a Peters back-projection operator according to the computationally perturbing. The reconstructing may include applying unmatched forward and back projections. Each detector signal of the plurality of detector signals may be obtained by directing an x-ray through the location at a different viewing angle.

According to various embodiments, a system for computed tomography (CT) image reconstruction is presented. The system includes at least one electronic processor that executes instructions to perform operations including: acquiring, by a detector grid of a computed tomography system, detector signals for a location within an object of interest representing a voxel, where each detector signal of a plurality of the detector signals is obtained from an x-ray passing through the location at a different viewing angle; reconstructing a three-dimensional representation of at least the object of interest, the three-dimensional representation including the voxel, where the reconstructing includes computationally perturbing a location of each detector signal of the plurality of detector signals within the detector grid, where the computationally perturbing corresponds to randomly perturbing a location of the x-ray within the voxel; and outputting the three-dimensional representation.

Various optional features of the above embodiments include the following. The reconstructing may include reconstructing according to a three-dimensional grid including the voxel and a plurality of other voxels, where each of the voxel and the plurality of other voxels has a same size. The reconstructing may include reconstructing according to a three-dimensional grid including the voxel and a plurality of other voxels, where the voxel and the plurality of other voxels include voxels of at least two different sizes. The voxel and the plurality of other voxels may consist of coarse voxels and fine voxels, where the object of interest is contained within the fine voxels. The acquiring, by the detector grid of the computed tomography system, the plurality of detector signals for the location within the object of interest may consist of acquiring less than 100 detector signals. The outputting may include displaying on a computer monitor. The randomly perturbing the location of the X-ray within the voxel may include relocating to a distance from a center of the voxel, where the distance is obtained from a statistical random distribution. The randomly perturbing the location of the X-ray within the voxel may include selecting a random direction from a center of the voxel. The operations may further include modifying a Peters back-projection operator according to the computationally perturbing. The reconstructing may include applying unmatched forward and back projections. Each detector signal of the plurality of detector signals may be obtained by directing an x-ray through the location at a different viewing angle.

BRIEF DESCRIPTION OF THE DRAWINGS

Various features of the embodiments can be more fully appreciated, as the same become better understood with reference to the following detailed description of the embodiments when considered in connection with the accompanying figures, in which.

DESCRIPTION OF THE EMBODIMENTS

Reference will now be made in detail to example implementations, illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

I. Introduction

Some embodiments utilize stochastic backprojection, disclosed herein, for three-dimensional image reconstruction. Prior art techniques that rely on sampling at fixed regular intervals may introduce artifacts due to the sampling interval interacting with the phase of the object of interest. Stochastic backprojection, as used in various embodiments, removes such periodicity, and with it, artifacts due to aliasing. Further, some embodiments produce such aliasing-artifact-free reconstructions in substantially less time than existing techniques. These and other features and advantages are disclosed in detail herein.

Figure 1:
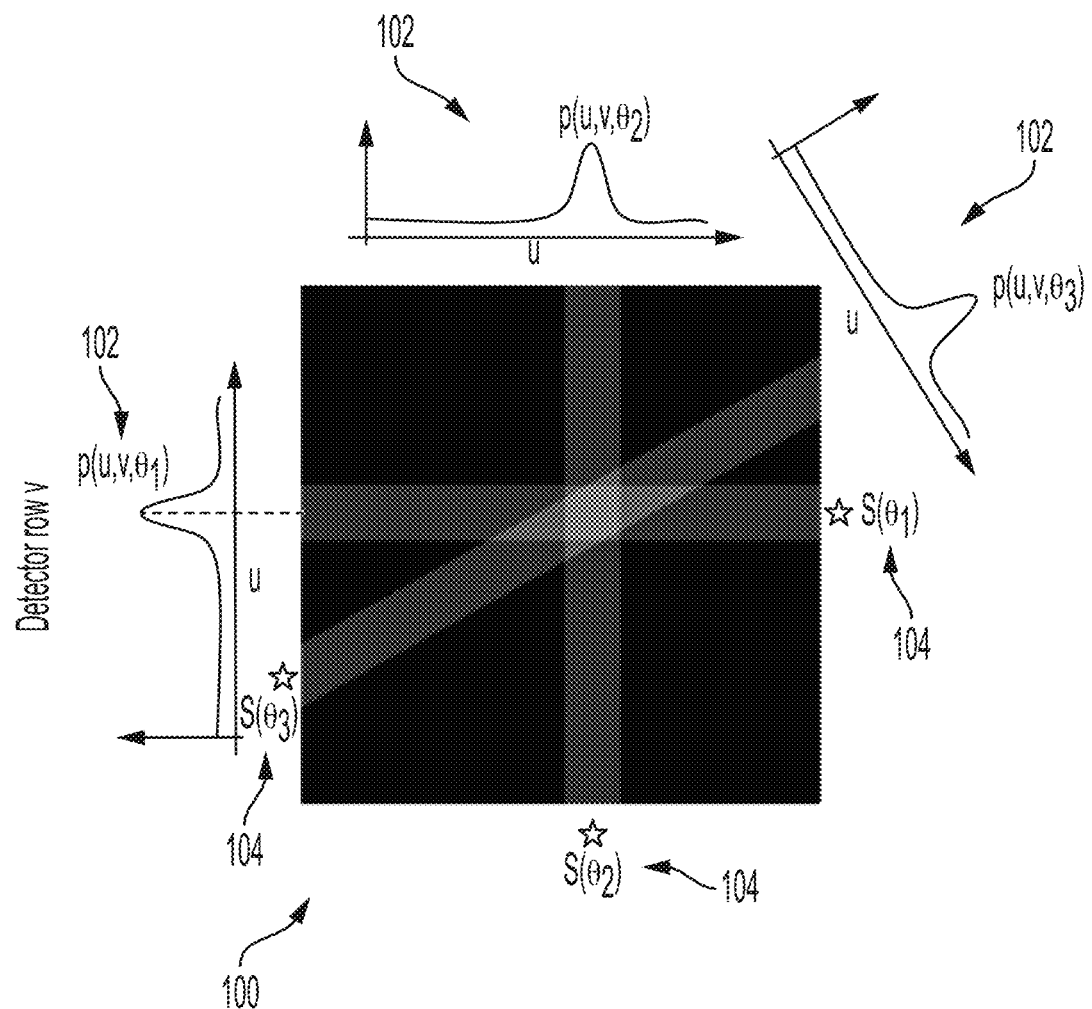
FIG. 1 is a schematic diagram depicting filtered backprojection.

FIG. 1 is a schematic diagram depicting filtered backprojection (FBP) 100. Certain three-dimensional elements are shown in two-dimensions for purposes of illustration rather than limitation. In general, CT images, particularly TCT images, are acquired using an x-ray source 104 and an opposing x-ray detector 102 that rotate around the subject to be imaged (for example, the patient). The x-ray source and detector may move separately or in solidarity, supported by an imaging gantry, and following a circular trajectory or a more complicated trajectory not describing a circle. An object of interest, such as a human body part, is placed within the gantry, and the detector 102 acquires signals at a variety of "view angles" (represented by $\theta i$) for each voxel to be imaged within the object of interest. The detector 102 may be in the form of a two-dimensional grid of detector elements. Note that for ECT, an x-ray source may be omitted, and instead the detector may detect radiation emitted from an injected radioisotope.

X-ray CT (e.g., axial, helical, and cone-beam) employs backprojection as the basic computational method to relate two-dimensional detector signal values from each projection to the image voxel values in the three-dimensional image reconstruction. FIG. 1 shows detector 102 signal, denoted pat detector coordinates (u, v) and angular coordinate $\theta$, related to the image voxel value by backprojection along a ray from the detector 102 position (u, v, $\theta$) to the x-ray source 104 position. Note that the detector signal p(u, v) may be subject to numerous well-known image processing techniques, including normalization, logarithmic scaling, and filtering.

This process is well-established in CT image reconstruction, the most common being various forms of three-dimensional FBP that represent the most common means of CT image reconstruction.

Figure 2:
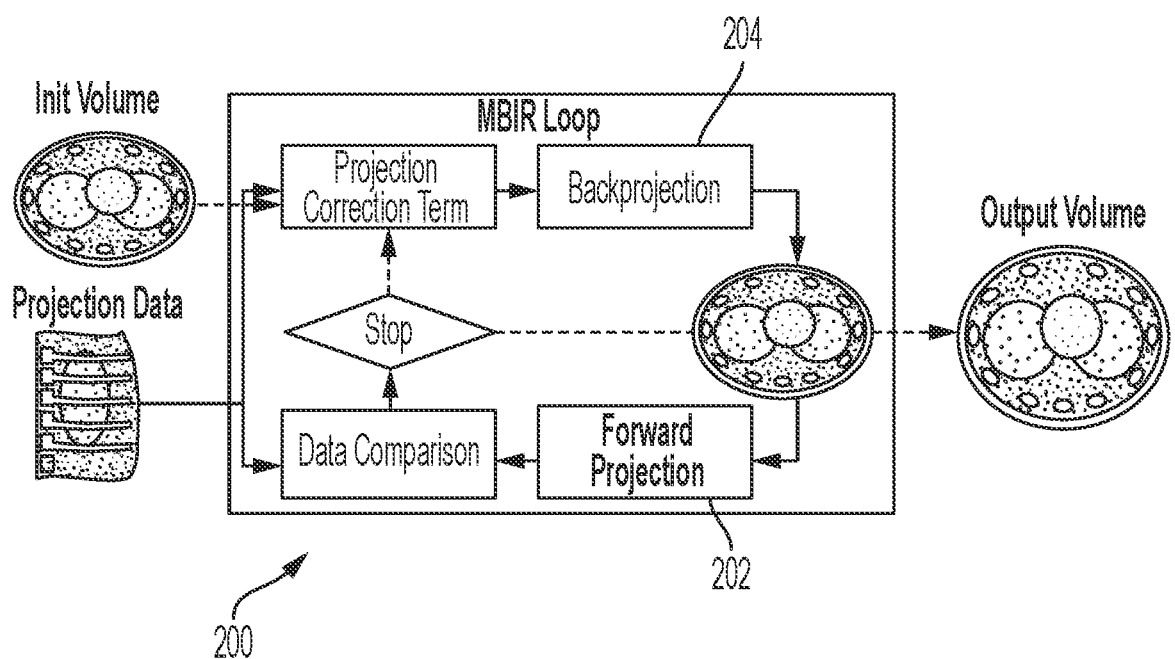
FIG. 2 depicts a flow diagram for iterative optimization in model-based image reconstruction.

FIG. 2 depicts a flow diagram 200 for iterative optimization in model-based image reconstruction (MBIR). Aside from FBP, various other methods for three-dimensional image reconstruction have been developed that offer improved noise-resolution tradeoffs in comparison. For example, MBIR yields better noise-resolution tradeoffs and artifacts reduction compared to analytic reconstruction methods like FBP. However, MBIR carries a major increase in computational burden due to several factors, including the iterative optimization that is involved with such approaches (often called iterative reconstruction).

As illustrated in FIG. 2, iterative optimization in MBIR involves repeated forward projection 202 of the current image estimate (typically denoted $\hat{\mu}(x,y,z)$) and backprojection 204 to compute the image (typically denoted $\mu(x,y,z)$) that minimizes an objective function (related to the difference between the forward-projected estimate to the measured data p(u,v)). Like FBP, MBIR is performed for each voxel that is reconstructed. A typical image may have 512 slices, with each slice partitioned into a 512×512 grid, for a total of 512×512×512=134,217,728 voxels. The process of repeated forward projection and backprojection for each voxel contributes to the computational burden and long runtimes that are common in MBIR.

"Matching" of the forward projection and backprojection calculation refers to the basis upon which the 3D image is reconstructed—e.g., rectangular voxels of dimension $a_x$, $a_y$, $a_z$—such that the forward-projected detector signal is computed in a manner that accurately reflects the system geometry and measured detector signal. Mathematically, forward projection and backprojection can be implemented as matrix operators acting on the vector (e.g., row ordered p(u,v)) of acquired projection data. Both matrix operators are considered to be "matched" when one is exactly the transpose of the other. An example of (approximately) well-matched forward projection and backprojection operators is the separable footprints design for both forward and backprojection. Using well matched forward projection and backprojection helps to avoid image artifacts (e.g., deterministic patterns that present confounding noise in the image) that can arise from a mismatch in forward projection and backprojection sampling. However, accurate forward projection—as with the separable footprints method—carries a high computational cost which, combined with iterative optimization, further contributes to the long runtimes of MBIR.

This increase in computation time can be partially alleviated with a combination of simple forward projection and back projection operators (e.g., simpler than the separable footprints forward and back projector). Example simplified projection methods include ray-driven operators for forward projection, such as the Siddon projector, coupled to voxel-driven backprojectors, such as the Peters linear interpolation backprojection operator. Although such simplified projection operators carry reduced computational burden, they invite "mismatch" of the forward projection and backprojection process that can degrade the quality of the three-dimensional image reconstruction artifacts and/or introduce noise.

As set forth herein, some embodiments overcome the effect of mismatched forward projection and back projection operators in three-dimensional image reconstruction, allowing the use of simplified forward and back projection operator combinations (with associated benefits to runtime) with minimal degradation in three dimensional image quality. Embodiments are generally beneficial to any three-dimensional image reconstruction techniques involving forward projection and backprojection, such as MBIR.

Some embodiments are particularly beneficial in scenarios in which the voxel size of the resolution grid differs from the "effective" pixel size of the acquisition geometry (i.e., the detector pixel size divided by the system geometrical magnification factor, that is, in three-dimensions, the voxel size at the object of interest). Such scenarios include the use of arbitrary voxel sizes appropriate for a particular imaging task, but not necessarily equal to the system effective voxel size. For example, such scenarios may involve larger voxel size to increase contrast resolution (reduce noise) at the cost of spatial resolution, which is a common scenario in imaging of low-contrast soft tissue structures.

Some embodiments are also beneficial for reconstruction techniques based on multi-resolution MBIR approaches that involve coarse and fine regions in the three-dimensional image reconstruction with minimal penalty in runtime. (Multi-resolution MBIR may be used to give improved spatial resolution in a finely sampled region of the image and/or to expand the volume of reconstruction to include a coarsely sampled outer region to cover the full object, e.g., to avoid "truncation" effects.)

Conventionally, the use of simple forward projection and backprojection operators in multi-resolution reconstruction results in undersampling artifacts generated in the coarse resolution region that propagate to the fine-resolution region with each iteration. Some embodiments use a modified backprojection operator that overcomes the deterministic undersampling pattern in conventional methods by including a random (e.g., stochastic) perturbation of the x-ray direction at each voxel in the 3D image reconstruction and for each projection angle. Such a modified backprojection operator results in an effective blurring of undersampling artifacts, with minimal penalty in computational burden.

The use of the novel backprojection operator disclosed herein according to various embodiments is referred to as "stochastic backprojection" (SBP). Results disclosed herein demonstrate that the SBP strategy reduces artifacts and yields an accurate 3D image reconstruction. For example, equivalent image quality was obtained using SBP compared to the separable footprint (SepFoot) matched forward and back projector, with 3.3× lower runtime. In the case of multi-resolution reconstruction, embodiments achieved a ten-times reduction in a root-mean-squared error (RMSE). Specifically, RMSE=$7.3 \times 10^{-5}$ mm$^{-1}$ for SBP, compared to $7.4 \times 10^{-4}$ mm$^{-1}$ for the conventional Peters backprojection operator. The RMSE obtained with SBP is comparable to that achieved using matched SepFoot forward and back projectors in the coarse resolution region ($7 \times 10^{-5}$ mm$^{-1}$), but with 25% lower runtime (96 seconds vs 127 seconds), and a six-times reduction in runtime when compared to using SepFoot for both the coarse and fine resolution regions.

II. Stochastic Backprojection

As presented above, MBIR offers numerous image quality advantages for CT and cone-beam CT as compared to analytical reconstruction, including better noise-resolution tradeoffs and superior image quality in scenarios susceptible to cone-beam artifact, data truncation, or sparse sampling. However, MBIR methods carry significant computational burden, leading to long reconstruction time.

An important strategy to alleviate MBIR computational burden is to use simple forward projection and backprojection models with the minimal runtime but accurate enough to generate images free of sampling-related artifacts or image quality degradation. The use of simple projection models coupled to reconstruction of the minimum number of voxels can result in dramatic reduction of computation time. Reduction of the number of voxels to reconstruct is achieved by performing the reconstruction with minimal field of view size, and maximal voxel size practically appropriate for the specific imaging task. The appropriate voxel size is therefore tied to particular imaging tasks and can greatly differ from the effective voxel size of the system. The use of arbitrary voxel sizes with simple, unmatched forward and backprojectors results in artifacts arising from deterministic inconsistencies between the sampling patterns for the forward and backprojection operations.

Another intuitive approach to reduce MBIR computational burden is to only reconstruct a partial region of the volume over a particular region of interest. However, partial volume reconstruction is susceptible to severe truncation artifacts in MBIR, and the full object (as well as supporting elements, such as a head frame, CT couch, or operating table) must be covered in the reconstructed volume.

A multi-resolution approach using SBP embodiments described herein is therefore able to mitigate the effects of large (truncated) objects with minimal computational burden. However, the combination of multi-resolution reconstruction with simple projectors, using only linear or point-like sampling approaches (e.g., not taking into account the actual volumetric footprint of the voxels) often results in artifacts arising from the use of a deterministic undersampling pattern in the coarse-resolution volume. These artifacts spread into the fine-resolution volume with increasing iteration number. The SBP operator according to various embodiments (for example, applied in the coarsely sampled)

alters the voxel sampling position by random perturbation per individual voxel and projection angle. This novel sampling method breaks the regular, deterministic structure of the undersampling effects of mismatched forward projection and backprojection operators and mitigates the undersampling-induced image artifacts. This approach overcomes such artifacts and improves computational runtime compared to more elaborate backprojectors.

Thus, various embodiments may utilize SBP with MBIR. Initial testing of the SBP operator was exercised in MBIR using a known penalized weighted least squares method. Penalized weighted least squares reconstructions were obtained minimizing a cost function of the form:

$$\hat{\mu}=\arg_\mu \min \|A\mu-l\|_w^2+\beta R(\mu) \quad (1)$$

In Equation (1), $\hat{\mu}$ is the image estimate, A is the operator for linear projection, l are the measured line integrals, and W is the matrix of data weighting terms, set to the raw measurements. The regularization term $R(\mu)$ penalizes image roughness with a quadratic function acting on the first order difference of voxel values, computed using six nearest neighbors, weighted by the scalar $\beta$. The cost-function is minimized using the ordered-subsets separable quadratic surrogates (OS-SOS) method. In general, the quantity $\|A\mu-l\|^2$ represents the objective function, which is minimized. The term pi represents the current estimate for the minimization, and $A\mu$ represents the forward projection.

To reduce the computational complexity of MBIR, various embodiments may utilize unmatched forward projection and backprojection operators (e.g., a Siddon forward projection operator and a Peters backprojection operator modified to implement SBP). Such mismatched operators may produce a roughly five-fold speedup compared to matched SepFoot projectors.

While computationally more efficient, the use of unmatched forward and (conventional, unmodified) backprojection approaches results in artifacts arising from inconsistent sampling, more evident when the voxel size departs from the effective voxel size of the system. More accurate, matched, forward projection and backprojection approaches can avoid such sampling effects, but at the cost of increased computational burden. Thus, embodiments utilizing SBP allows the use of simpler (mismatched) forward projection and backprojection operators without sampling artifacts, by including a random perturbation of the voxel sampling position, as depicted in the simplified to two-dimensions illustration of FIG. 3.

Figure 3:
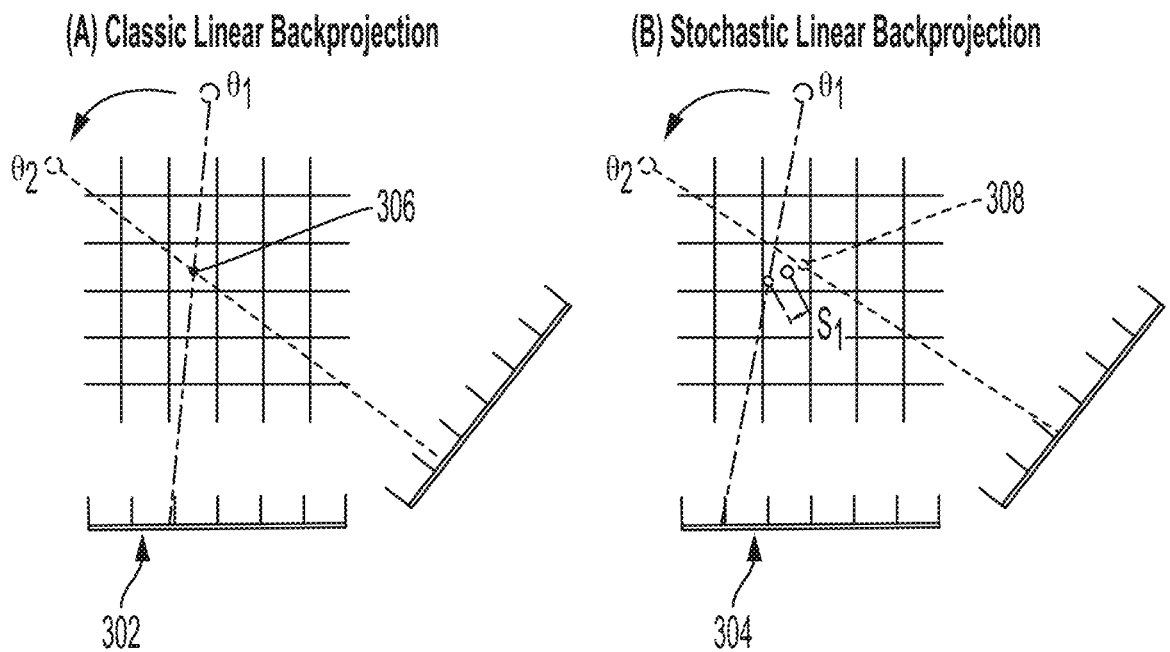
FIG. 3 is a schematic diagram of standard linear or "Peters" backprojection in comparison to stochastic backprojection according to various embodiments.

FIG. 3 is a schematic diagram of standard linear or "Peters" backprojection 302 in comparison to stochastic backprojection 304 according to various embodiments. (FIG. 3 depicts in two dimensions a process that occurs in three dimensions for purposes of illustration rather than limitation.) In particular, FIG. 3 depicts the classic approach for voxel-based Peters backprojection 302 with bilinear interpolation. Note that both depicted rays pass through the center of voxel 306. Using this approach in combination with multi-resolution volumes results in artifacts from inconsistent sampling of the low-resolution region (e.g., with coarse voxels, not matched to detector pixel size). By contrast, for stochastic backprojection 304, including a random, subvoxel, shift of the ray position inside each voxel and projection angle results in a modified sampling pattern that helps to alleviate sampling artifacts. Thus, FIG. 3 depicts such a subvoxel shift in voxel 308. Note that neither of the two depicted rays pass through the center of voxel 308. Rather, they are perturbed away from the center in a random direction by a random subvoxel amount, e.g., Si. For (coarse and fine) multi-resolution MBIR, the stochastic backprojection 304 operator is especially effective in combination with the smoothing effect of the coarse voxel size.

Figure 4:
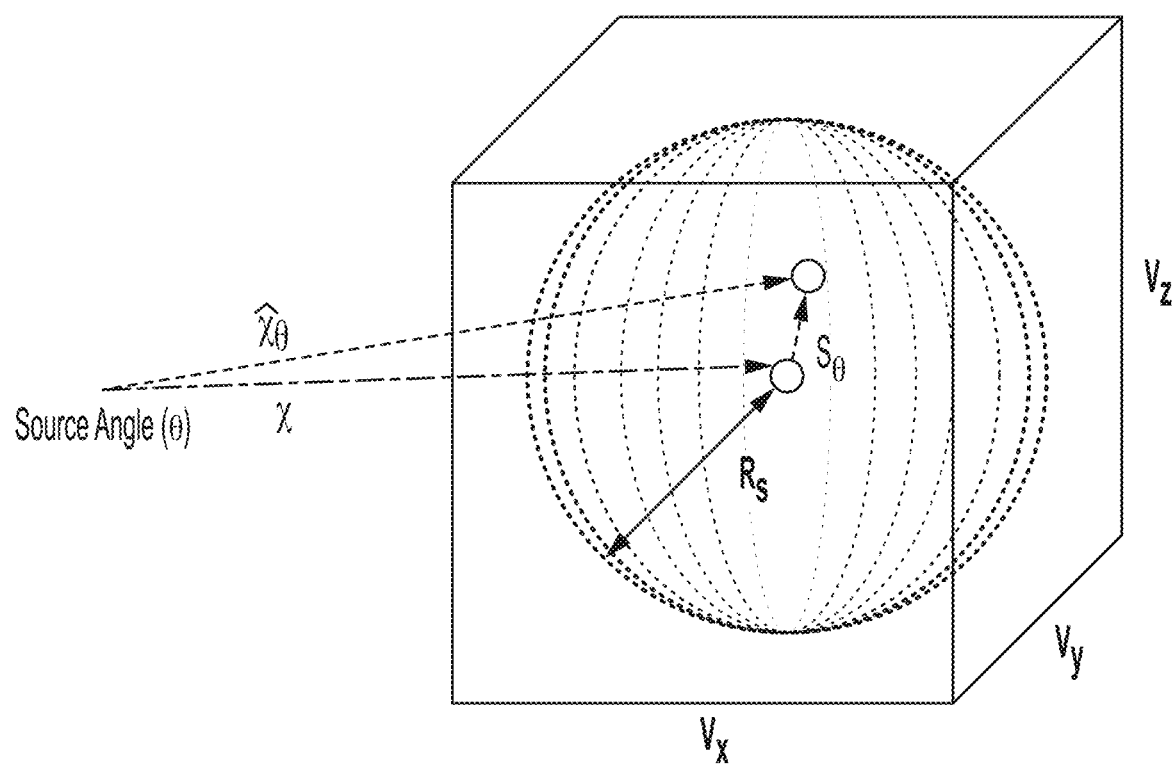
FIG. 4 is a schematic diagram depicting spherical support for three-dimensional stochastic perturbation of voxel sampling position according to various embodiments.

FIG. 4 is a schematic diagram depicting spherical support for three-dimensional stochastic perturbation of voxel sampling position according to various embodiments. Some embodiments utilize a modified Peters backprojection operator to alleviate the impact of sampling artifacts with minimal computational burden. The modified Peters backprojection operator computationally implements a random perturbation of the ray position inside each voxel for every ray traced in the reconstruction. This corresponds to and defines a random perturbation of the location within the detector (e.g., detectors 102 of FIG. 1) at which the ray is received. For projection angle $\theta$, the new ray intersect position ($\hat{x}_\theta$) for one individual voxel may be computed as, by way of non-limiting example:

$$\hat{x}_\theta = U(0,R_s) \cdot s_\theta + x \quad (2)$$

In Equation (2), $\hat{x}_\theta$ represents the perturbed ray position, $U(0, R_s)$ represents a uniformly distributed random number between 0 and the radius $R_s$ of a sphere contained by the voxel (setting the maximum deviation from the voxel center), $s_e$ is a uniformly generated unit-norm random vector describing the direction for the perturbation (i.e., voxel center shift), and x is the vector describing the original position (i.e., before the perturbation) of the center of the voxel. The value of $R_s$ may be tuned to achieve the desired balance between sampling perturbation and fidelity. Experiments performed by the inventors showed similar performance for a large range, from 0.3 $V_{x(yz)}$ to 0.5 $V_{x(yz)}$, i.e., from 0.3 of the smallest voxel radius to 0.5 of the largest voxel radius.

Note that Equation (2) is used to compute $A^{-1}$, where A is as represented in Equation (1). This is used for backprojection. The Peters backprojection operator represents a known technique for modeling $A^{-1}$. Some embodiments use Equation (2) to modify a Peters backprojection operator to represent random perturbations as shown and described herein. In some embodiments, the random offsets result in perturbing the sampling pattern of the detector positions to be backprojected on a given voxel. Note further that the term "random" as used throughout herein includes pseudorandom and other techniques that have properties of random distributions.

As described in detail herein, according to some embodiments, the perturbations may be applied on the backprojection operator. However, according to other embodiments, the random perturbation may be applied on the forward projection operation, or on both the forward projection operation and the backprojection operator.

Note that the perturbations of the ray position within a voxel may be performed computationally, e.g., using Equation (2), in silico rather than physically, e.g., by changing the actual direction of the x-ray beam. Advantages of computational perturbation include the lack of a need to alter CT hardware, which is expensive, time consuming, and potentially subject to approval by relevant medical governing bodies.

III. Results, Applications, and Implementations

Figure 5:
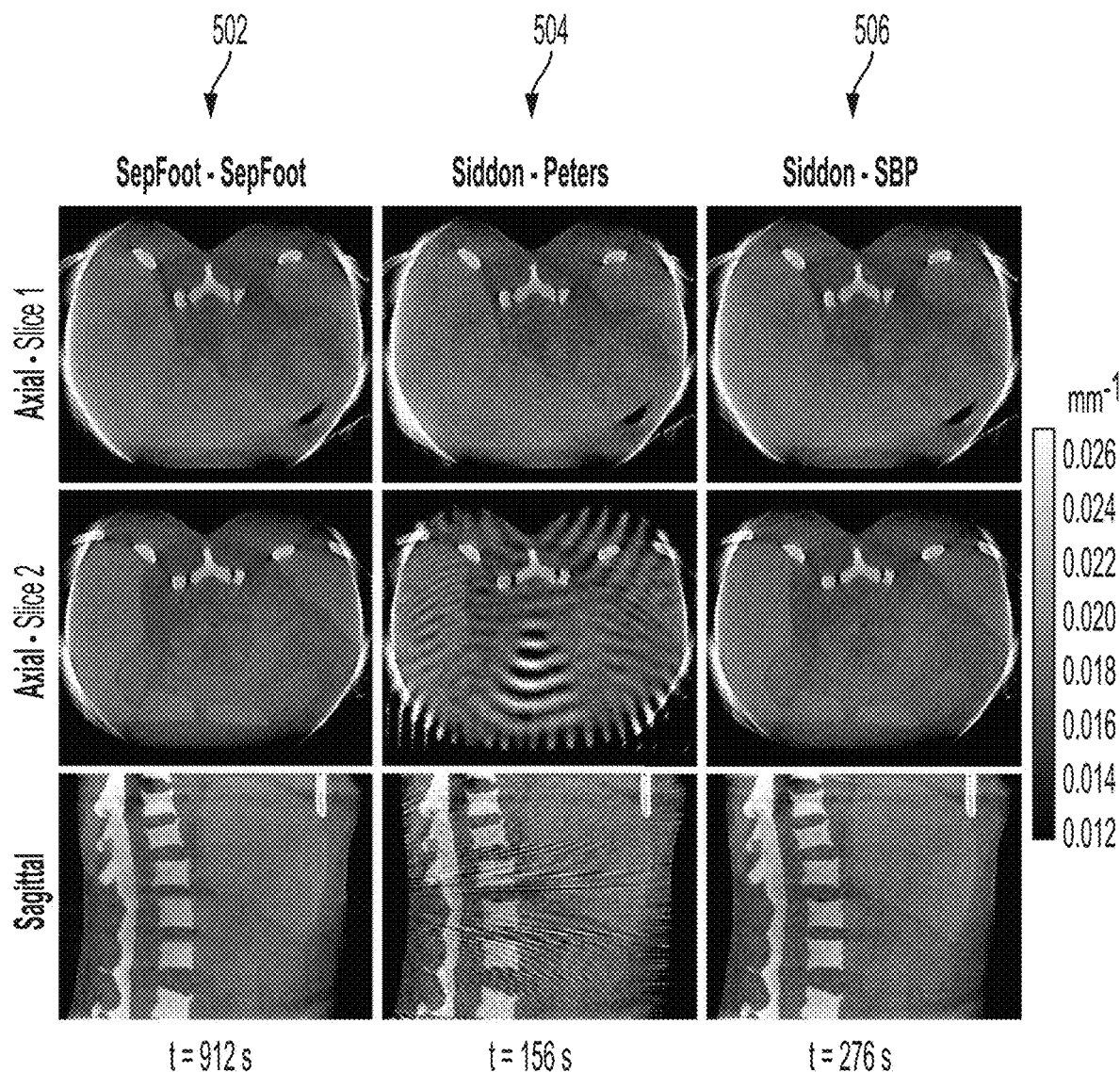
FIG. 5 illustrates images obtained using matched forward projection and backprojection, using unmatched forward projection and backprojection, and using unmatched forward projection and stochastic backprojection according to various embodiments.

FIG. 5 illustrates images obtained using matched forward projection and backprojection 502, using unmatched forward projection and backprojection 504, and using unmatched forward projection and stochastic backprojection 506 according to various embodiments.

In particular, FIG. 5 shows the full field-of-view reconstructions of cone beam CT images using SepFoot 502, Siddon with Peters 504, and Siddon with SBP. The reconstructions were obtained with a 0.5 mm voxel grid, while the effective voxel size of the system is 0.27 mm. When using simple, unmatched, projection operators 504, the reconstruction time is greatly reduced (912 seconds versus 156 seconds, a 5.8-fold reduction), but obvious artifacts are present, particularly in sagittal views and slices away from the central slice of the reconstructed volume. Even at the central slice, deviation between the reconstructed values and those obtained with matched SepFoot projection operators 502 can be observed (more obvious in difference images in FIG. 6, below). Application of the SBP projection operators 506 avoids the artifacts, for all areas in the image, with a 3.3 times reduction in reconstruction time compared to SepFoot 502.

Figure 6:
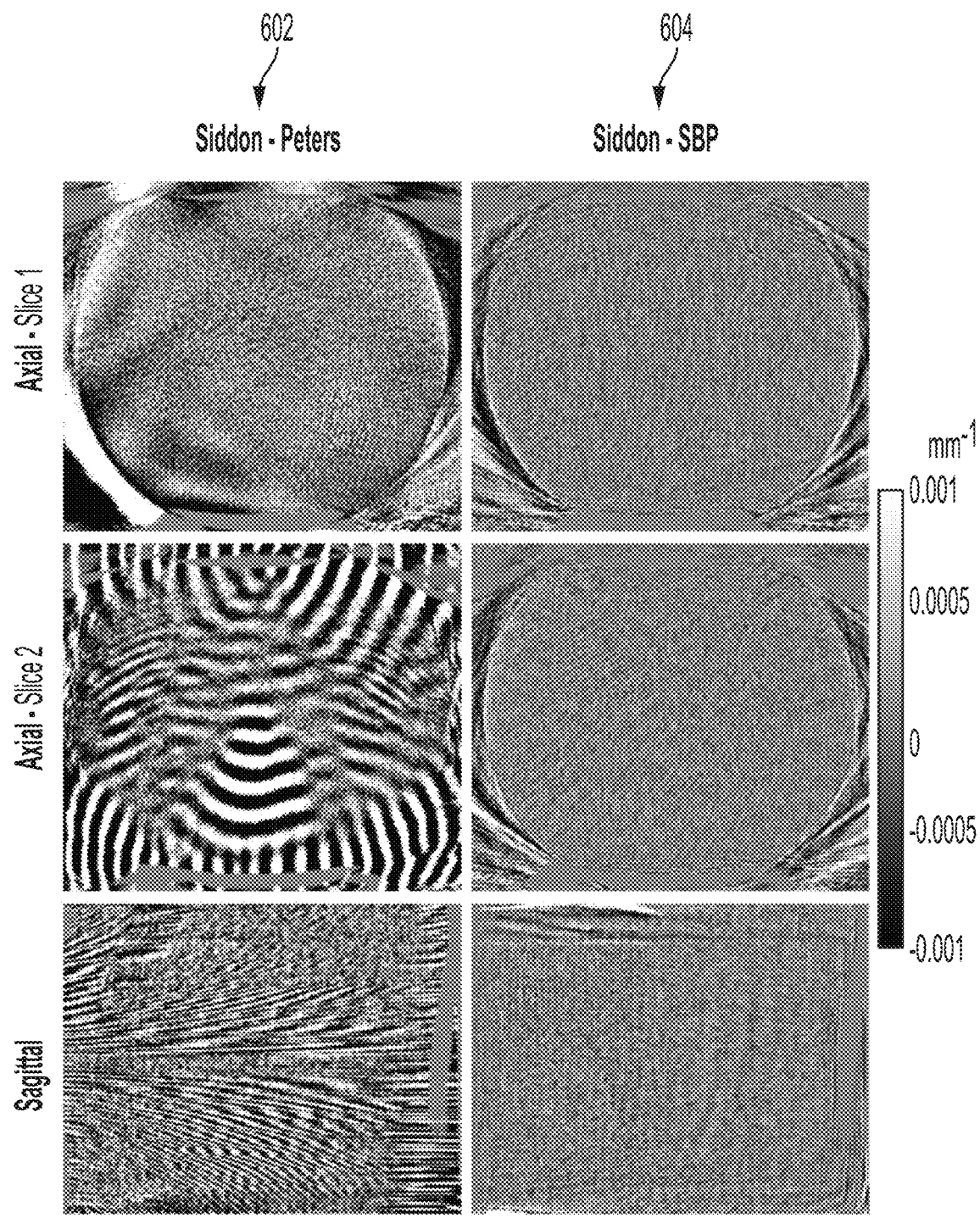
FIG. 6 depicts difference images quantifying deviations between images produced using matched forward projection and backprojection and unmatched forward projection and backprojection, and between matched forward projection and backprojection and unmatched forward projection and stochastic backprojection according to various embodiments.

FIG. 6 depicts difference images quantifying deviations between images produced using matched forward projection and backprojection and unmatched forward projection and backprojection, and between matched forward projection and backprojection and unmatched forward projection and stochastic backprojection according to various embodiments. In particular, FIG. 6 depicts difference images quantifying the deviation between reconstructions using matched versus unmatched SepFoot projection operators 602, and reconstructions obtained using matched forward projection and backprojection operators and a simple Siddon forward projector and a SBP Peters backprojection operator 604.

The difference images in FIG. 6 show the reduction in artifacts for the stochastic backprojection embodiment 604. Whereas unmatched conventional Siddon-Peters forward and backprojection 602 results in large errors (centered "Slice 1" and non-centered "Slice 2" axial planes in FIG. 6) indicating pronounced differences from the true image, the errors/artifacts were greatly diminished in the SBP embodiment 604, which exhibits only minor random differences from the true image due to perturbation in backprojection.

This disclosure now turns to a consideration of truncation and objects outside of the field of view. In practical imaging scenarios, the limited field-of-view of the imaging system (for example, a C-arm for 3D image-guided medical procedures) results in truncated volumes, and accessory positioning and holding devices (e.g., head holder, or patient couch) can fall outside of the detector field of view. This results in degradation of image quality arising from the effects of truncation on the reconstruction algorithm. In MBIR, where the complete support of the measured projections needs to be reconstructed, artifacts are particularly severe if the reconstructed volume is not large enough to accommodate all objects covered by the x-ray beam. However, extending the reconstruction field of view to include the complete object support often results in prohibitively large computational cost. (The effects of truncation on penalized weighted least squares image quality are illustrated in the example in FIG. 8, below. Comparison between full field of view reconstruction 802 and highly truncated, single-region, reconstruction 804 yielded strong truncation artifacts and dramatic image quality degradation.) To address this problem, some embodiments adapt a multi-resolution reconstruction approach, as depicted in FIG. 7.

Figure 7:
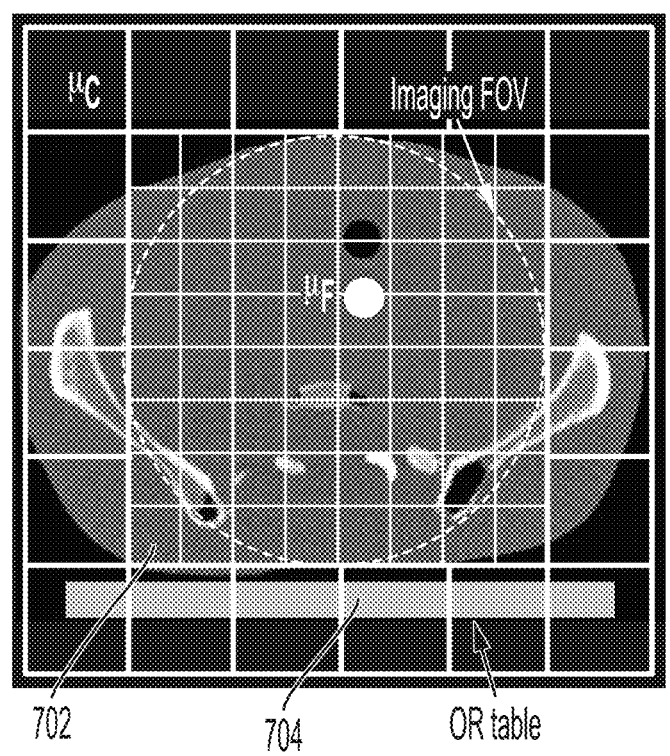
FIG. 7 is a schematic representation of a multi-resolution image according to various embodiments.

FIG. 7 is a schematic representation of a multi-resolution image according to various embodiments. In particular, FIG. 7 represents a schematic depiction of the multi-resolution method for extending the reconstruction field of view to cover the complete object support and the associated elements (e.g., an imaging table), with minimal increase in computational burden. The field of view is divided in regions of fine 702 and coarse 704 voxels with different regularization strengths ($\mu_f$ and $\beta_c$, respectively). The finely voxelized region 702 contains the object of interest, while the low-resolution, coarsely sampled, surrounding region 704, includes the partly truncated objects and external hardware. Due to the use of coarse voxelization 704 in the surrounding region, the increase in computational burden (speed and/or memory) associated with reconstructing a large volume is mitigated.

Figure 8:
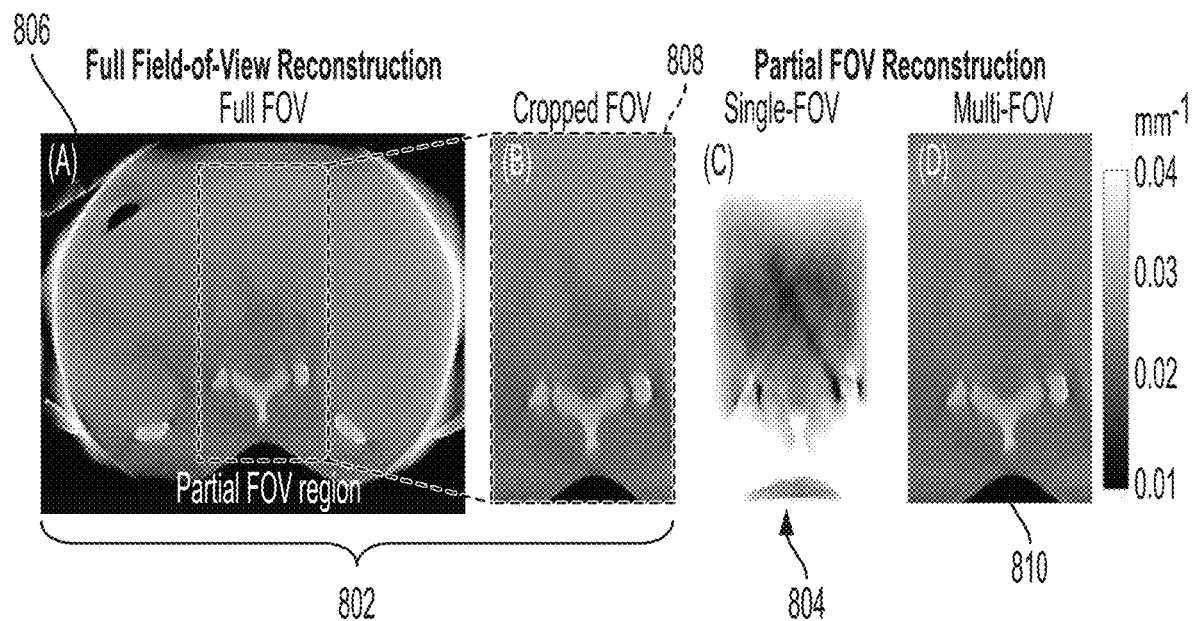
FIG. 8 depicts various field of view relative to objects of interest according to various embodiments.

When applying the multi-resolution, multi-field-of-view technique, truncation artifacts are greatly mitigated and the image quality is visually equivalent to the full-field-of-view reconstruction, as depicted in FIG. 8.

FIG. 8 depicts various fields of view relative to objects of interest according to various embodiments. In particular, FIG. 8 depicts an example cone beam CT volume reconstructed with the full-field-of-view covering the complete object and accessory elements 806, and zoom-in region 808. When reconstructing a volume size equivalent to the zoom-in region in 808, severe quality degradation is observed due to truncation artifacts at 804. Application of the multi-resolution, multi-field-of-view, reconstruction per 810 results in image quality comparable to the full-field-of-view reconstruction. Accelerating such multi-resolution reconstruction, multi-field-of-view methods to faster runtimes benefits SBP by avoiding artifacts associated with mismatched simple forward and backprojectors.

A multi-resolution approach is therefore valuable to overcoming truncation effects. In such an approach, SBP allows incorporation of simplified (mismatched) forward projection and backprojection operators to speed runtime without artifacts that would normally be incurred by the mismatch.

Figure 9:
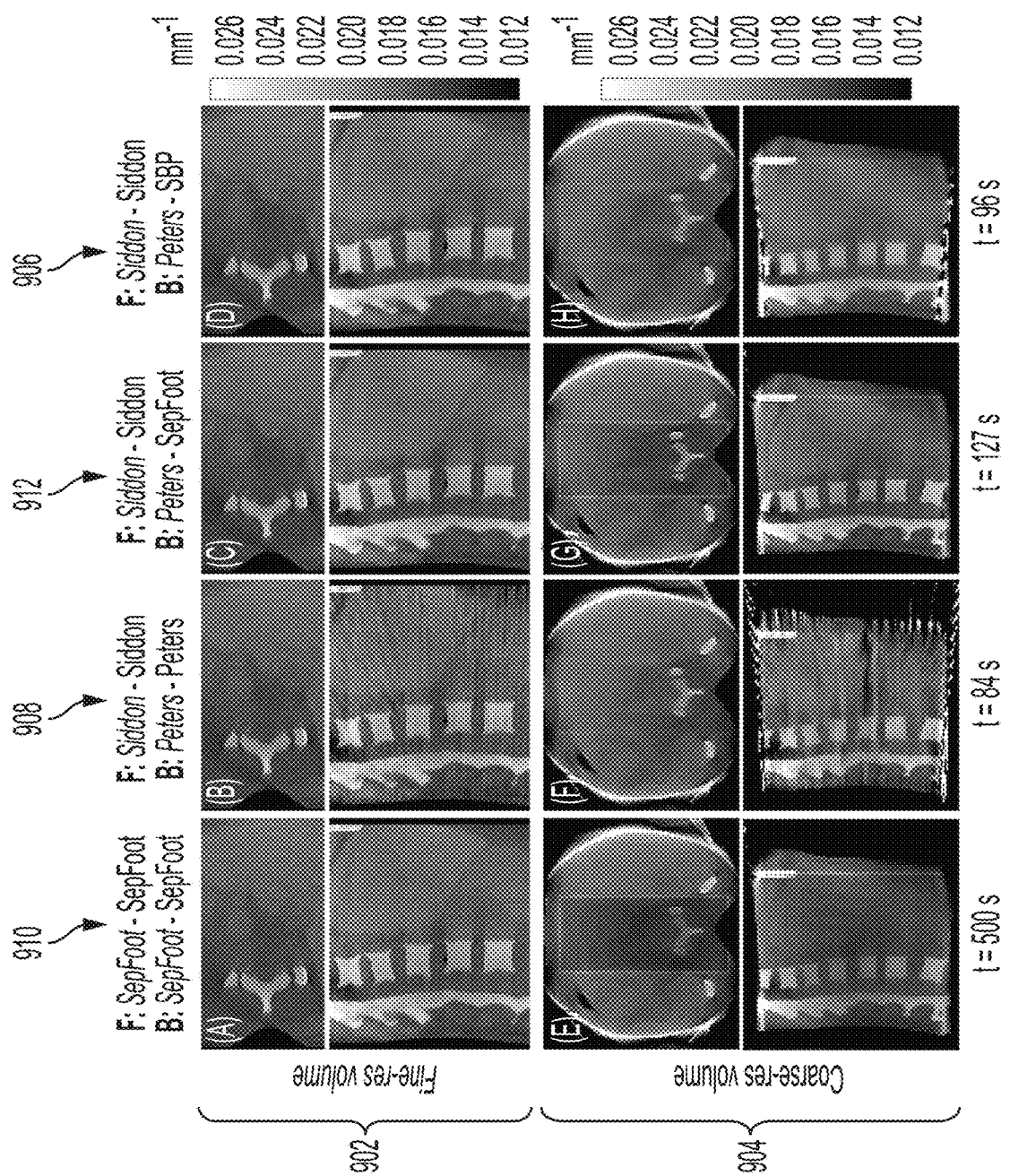
FIG. 9 illustrates various fine and coarse resolution regions obtained using various image reconstruction techniques, according to various embodiments.

FIG. 9 illustrates various fine resolution regions 902 and coarse 904 resolution regions obtained using various image reconstruction techniques, including according to various embodiments. The images in FIG. 9 are labeled to indicate the respective forward projection and backprojection operators used for the fine resolution and coarse resolution image portions. The labels are of the form, "X: [fine resolution]-[coarse resolution]", where X may be "F" for forward projection or "B" for backprojection, and where [fine resolution] and [coarse resolution] indicate the respective operators (note that the fine resolution operators are indicated by italics). In particular, FIG. 9 shows a comparison in terms of artifacts and reconstruction time between: an approach using a combination of the Siddon forward projection with Peters backprojection for the fine resolution volume and the Siddon forward projection and the proposed stochastic backprojector for the coarse resolution volume 906, an approach using unmodified simple forward and backprojectors 908, and approach employing the SepFoot forward and backprojectors for all operations 910, and an approach using a combination of the Siddon forward projection with Peters backprojection for the fine resolution volume and the Siddon_forward projection with separable footprints backprojection for the coarse resolution volume 912.

The experiments were performed using a highly truncated fine-resolution volume. The SBP embodiment 906 achieved images virtually free of artifacts with a 1.15× larger reconstruction time compared to unmodified approach 908, compared to a 1.5× reconstruction time for the combination of Siddon, Peters, and separable footprints 912, and to 6× larger reconstruction time for the separable footprint approach 910.

Note that use of the fastest forward (Siddon) and backprojector (Peters) for both the fine and coarse resolution regions results in artifacts in the fine resolution volume (A), arising from inconsistent sampling in the coarse resolution region (E). Artifacts can be suppressed when using accurate, matched, forward and backprojectors (separable footprints), for both the fine (B) and coarse (F) resolution volumes, at the price of six-fold longer reconstruction time. Alternatively, artifacts can be alleviated by replacing the simple Peters backprojection operator in the coarse resolution region (G) by a separable footprints backprojection operator, while using simple forward and backprojectors for the rest of the operations (C), with ~50% longer reconstruction time. Using an SBP embodiment on the coarse volume backprojection resulted in the suppression of sampling artifacts in the fine resolution volume (D), and a noticeable reduction of them in the coarse resolution volume (H). The SBP embodiment yielded a 25% shorter reconstruction time than the next fastest option, offering the lowest time penalty (14%) of the explored options.

Figure 10:
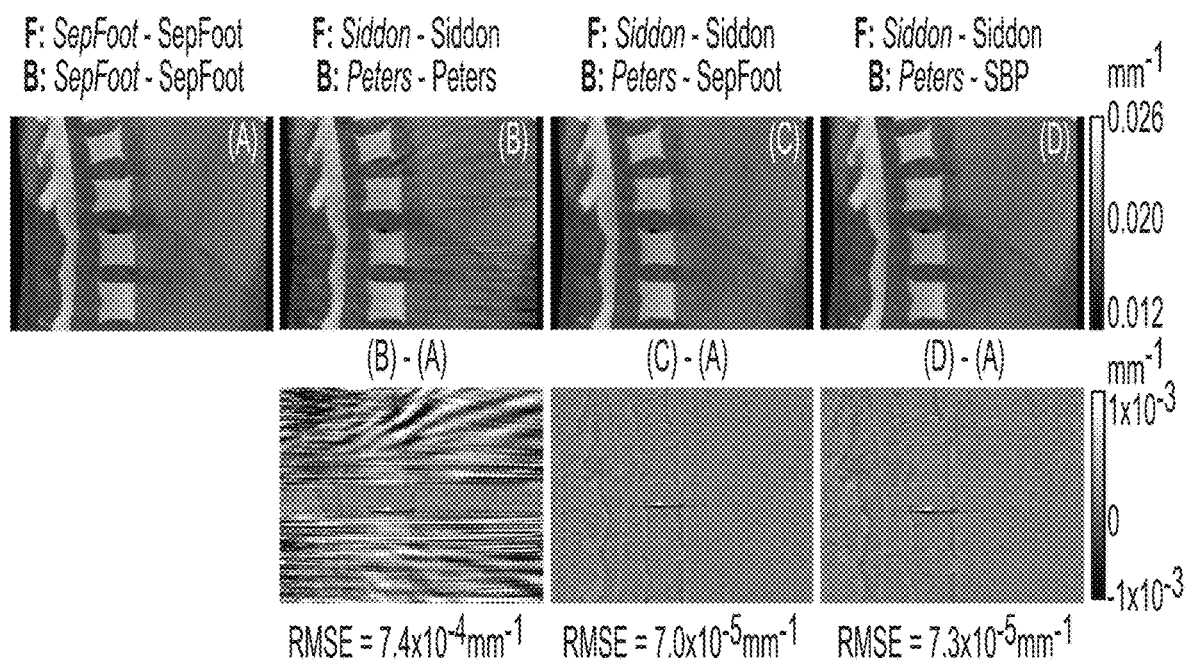
FIG. 10 depicts quantifications of difference in reconstructions obtained using various image reconstruction techniques, including according to various embodiments.

FIG. 10 depicts quantifications of difference in reconstructions obtained using various image reconstruction techniques, including according to various embodiments. In particular, FIG. 10 depicts quantification of difference in reconstructions obtained with accurate, matched forward and backprojectors using separable footprints (A) and the fastest forward projection operator (Siddon) and backprojection operator (Peters) (B), the combination of the simple Peters backprojector in the fine resolution region with a separable footprints backprojector in the coarse resolution region (C), and the combination of the simple Peters backprojector in the fine resolution region with the proposed stochastic backprojector in the coarse resolution region (D). Difference images and root mean squared error values in the bottom row show very similar performance in terms of artifact suppression and ~10× reduction in RMSE for approaches using separable footprints and the proposed stochastic projector, with much lower computational burden for the stochastic projector.

The data depicted in FIG. 10 also quantifies the image accuracy between three-dimensional image reconstructions obtained with matched separable footprint forward projection operators and backprojection operators and with the different combinations of simple forward and backprojectors, measured as RMSE and difference images. Difference images show significant artifacts and large RMSE when using the simple forward and backprojectors (B). When replacing the backprojection operator in the coarse resolution region by a separable footprints model (C), difference images showed only minor differences and no significant artifacts, reducing RMSE to ~10% of the value in (B). Use of the SBP embodiment (D) resulted in similar reduction of artifacts and RMSE compared to the SepFoot model (A), but with 25% lower reconstruction time.

Figure 11:
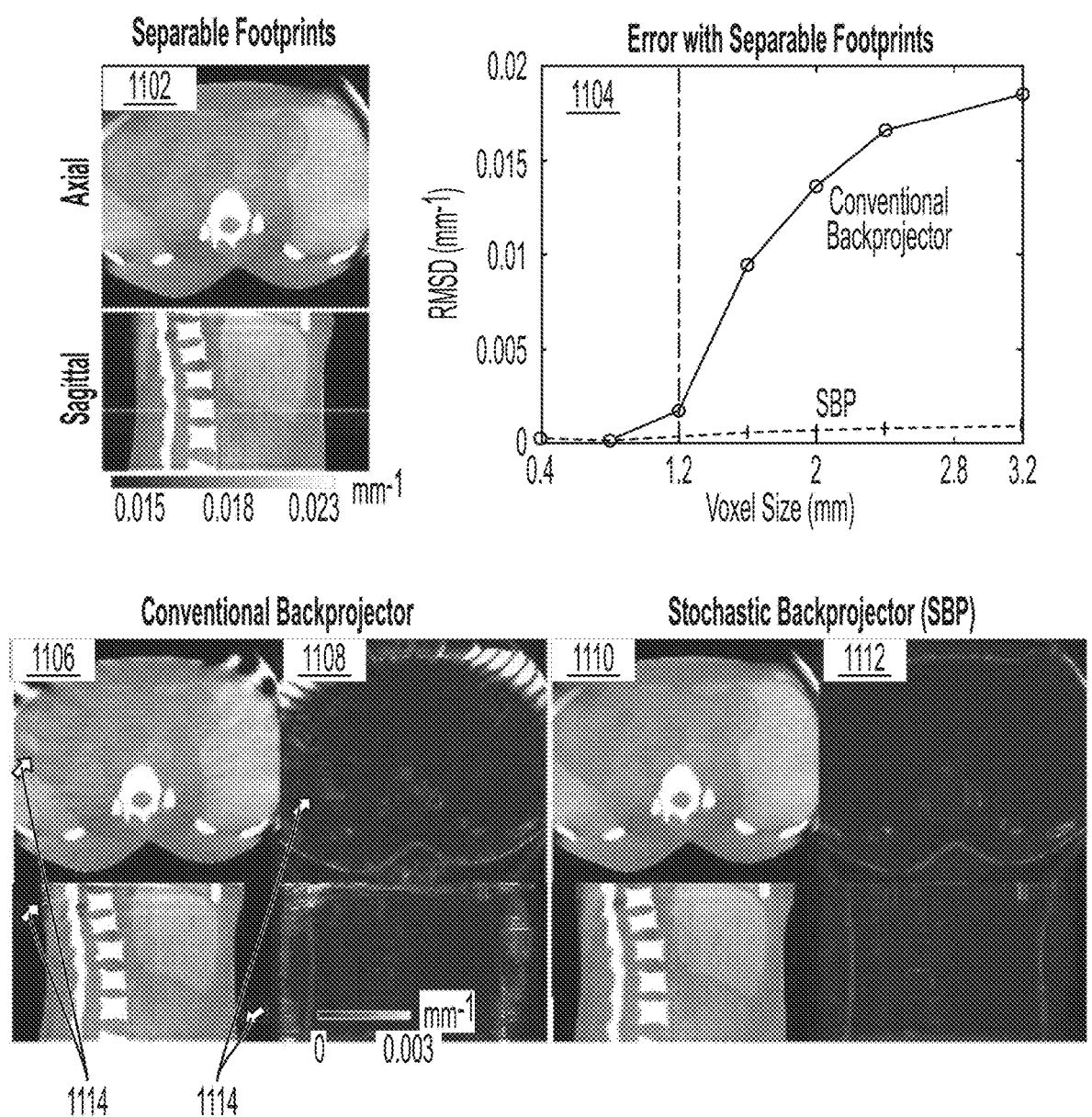
FIG. 11 depicts comparisons between volumes reconstructed with separable footprints, the conventional Peters backprojector, and the stochastic backprojection.

FIG. 11 depicts comparisons between volumes reconstructed with separable footprints (image 1102), the conventional Peters backprojector (image 1106), and the stochastic backprojection (image 1110). Each image was reconstructed using a single resolution penalized weighted least squares method with no acceleration techniques for increasing voxel size. The error (root-mean-square difference, RMSD) is seen to increase sharply with voxel size using a conventional backprojector, but the error remains low using the stochastic backprojector (SBP).

Image 1102 depicts axial and sagittal slices of a reconstruction of an abdomen phantom obtained using a single resolution approach (1.2 mm isotropic voxel size). Image 1106 depicts undersampling with mismatched forward and backprojectors manifests as dark-bright modulation of the reconstructed values (see arrows 1114), also evident in the difference image 1108, which depicts the difference between image 1106 and image 1102. Difference image 1112, which depicts the difference between image 1110 and image 1102, further shows that the stochastic backprojector reduced or eliminated sampling artifacts, resulting in a noticeably lower difference.

The use of unmatched conventional projectors resulted in deterministic sampling inconsistencies that yielded noticeable artifacts for voxel sizes departing from the effective voxel size for the system, as illustrated by the axial and sagittal slices for a voxel size of 1.2 mm (image 1106) when compared to their separable footprints counterpart (image 1102), with difference image (1108) showing errors of ~15% the total attenuation in soft-tissue regions. The reconstructions obtained with stochastic backprojection (image 1110) revealed a marked reduction of the artifacts achieved through the more favorable sampling achieved by the randomly perturbed sampling pattern.

Graph 1104 depicts root-mean-square deviation between volumes obtained with separable footprints (e.g., image 1102) and volumes reconstructed with the conventional Peters backprojector and with the stochastic backprojector (e.g., image 1110), as a function of voxel size. Graph 1104 thus quantifies the severity of the artifacts, showing a strong increase in root-mean-square deviation for voxel sizes larger than the effective voxel size, spanning more than one order of magnitude within the explored voxel size range (root-mean-square deviation=$1.5 \times 10^{-3}$ mm-1 at 1.2 mm voxels, to $1.9 \times 10^{-2}$ mm-1 at 3.2 mm voxels). The stochastic backprojection suppressed aliasing effects and yielded a nearly flat root-mean-square deviation curve across the full range of voxel sizes.

Figure 12:
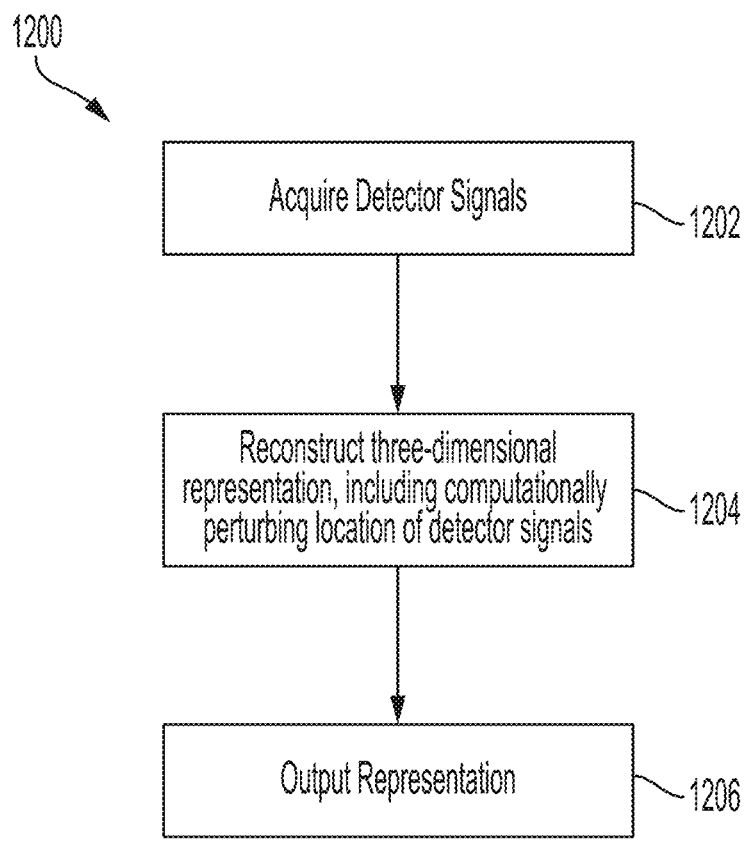
FIG. 12 is a flowchart for a method of image reconstruction according to various embodiments.

FIG. 12 is a flowchart for a method 1200 of image reconstruction according to various embodiments. Method 1200 may be implemented using a system disclosed herein, e.g., system 1300 as shown and described below in reference to FIG. 13.

At 1202, method 1200 acquires a plurality of computed tomography detector signals for a location with an object of interest at a detector grid. The location within the object of interest may represent a single voxel. According to various embodiments, each detector signal of the plurality of detector signals may be obtained by passing an x-ray through the location at a different viewing angle, e.g., as a TCT source and detector grid rotate about the object of interest. According to various embodiments, each detector signal of the plurality of detector signals may be obtained from an x-ray passing through the location at a different viewing angle, e.g., as an ECT detector grid or x-ray source rotates about the object of interest.

At 1204, method 1200 reconstructs a three-dimensional representation of at least the object of interest using the data resulting from 1204. The three-dimensional representation includes the voxel of 1202, and may include many additional voxels so as to form a full three-dimensional representation of the object of interest, possibly including additional objects. The reconstructing includes computationally perturbing a location of each detector signal of the plurality of detector signals within the detector grid. Such computational perturbation corresponds to randomly perturbing a location of the x-ray within the voxel, e.g., as shown and described above in reference to FIGS. 3 and 4. The reconstruction may proceed through the use of weighted data values according to known techniques. For example, the contribution from each angular projection (i.e., from each backprojected ray, one per value of view angle θ) may be added, possibly weighted by terms dependent on the geometrical configuration of the scanner (e.g., dependent on the distance between the particular voxel and the source/detector).

At 1206, method 1200 outputs the representation. The output may be to a computer monitor, to persistent storage, to a network-connected device (e.g., over the network), or to an automated diagnostic system, according to various embodiments.

Figure 13:
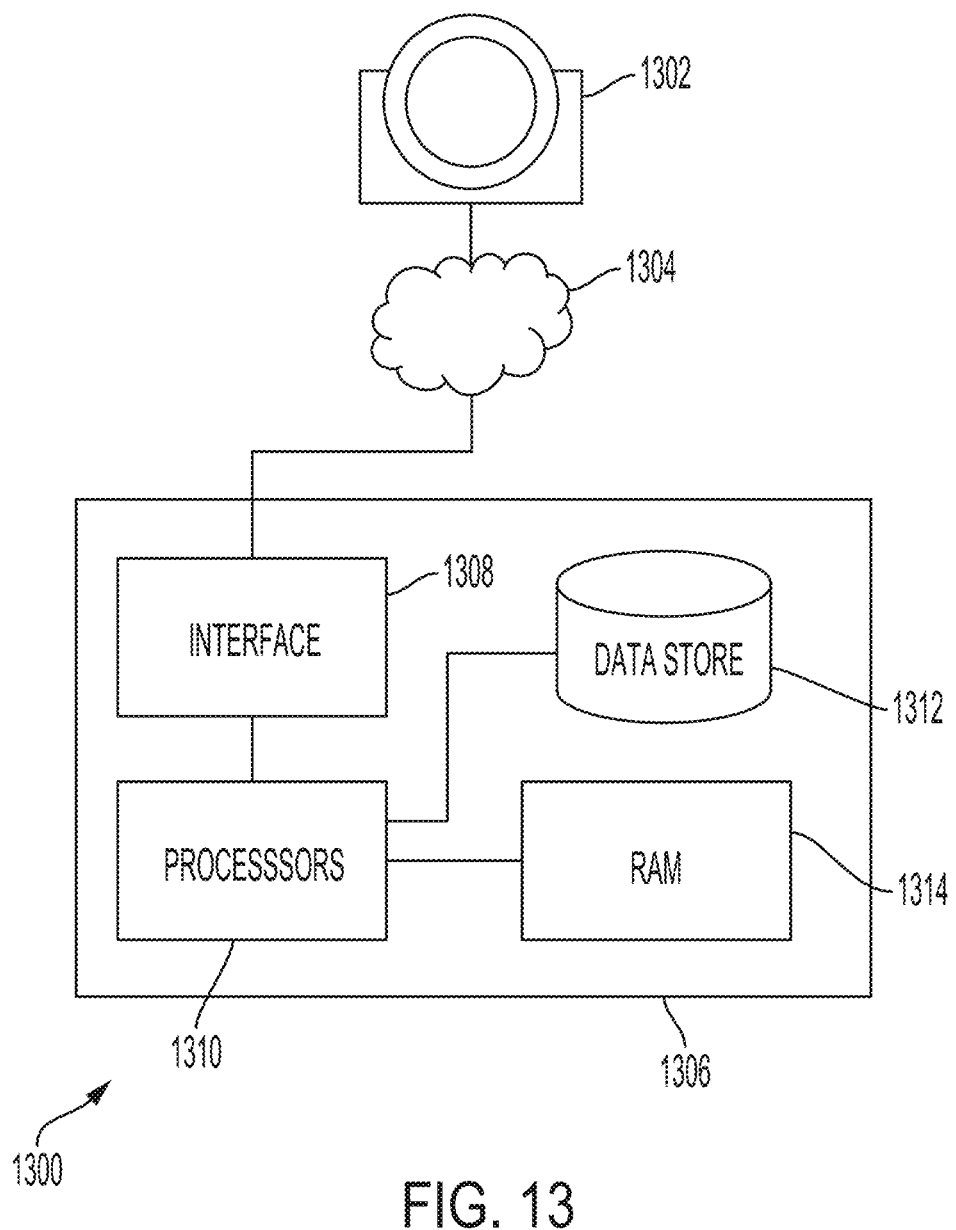
FIG. 13 is a schematic diagram for a system for implementing a method of image reconstruction according to various embodiments.

FIG. 13 is a schematic diagram for a system 1300 for implementing a method of image reconstruction according to various embodiments. System 1300 includes CT scanner 1302, which includes a CT gantry. CT scanner 1302 may by any of a variety of CT scanners, including without limitation axial, helical, and cone-beam. Further, CT scanner 1302 may be a TCT scanner or an ECT scanner (e.g., PET, SPECT). CT scanner 1302 is communicatively coupled to computer system 1306, either directly or via network 1304, as shown. Computer system 1306 includes input interface 1308 at which data representing detector events is received. Input interface 1308 is communicatively coupled to one or more processors 1310.

Processors 1310 are communicatively coupled to random access memory 1314 operating under control of or in conjunction with an operating system. The processors 1310 in embodiments may be included in one or more servers, clusters, or other computers or hardware resources, or may be implemented using cloud-based resources. The operating system may be, for example, a distribution of the Linux™ operating system, the Unix™ operating system, or other open-source or proprietary operating system or platform. Processors 1310 may communicate with data store 1312, such as a hard drive or drive array, to access or store program instructions and other data. Processors 1310 may, in general, be programmed or configured to execute control logic and control operations to implement methods disclosed herein, e.g., method 1200. Other configurations of computer system 1300, associated network connections, and other hardware, software, and service resources are possible.

In sum, this disclosure presents a novel system for, and method of, reconstructing three-dimensional computed tomography images that utilize stochastic backprojection. The stochastic backprojection technique permits the use of simplified, mismatched forward projection operators and backprojection operators in three-dimensional image reconstruction for faster runtime without the image quality degradation suffered with conventional backprojectors. Embodiments may be used for both iterative reconstruction (including the use of unmatched forward/backprojectors) analytical reconstruction methods (including only one single backprojection and no forward projection operator). In particular, embodiments are applicable to MBIR, both single resolution and multi-resolution. Further, embodiments are also beneficial for other reconstruction methods, e.g., conventional FBP, under conditions that introduce artifacts, for example, view sampling effects in reconstruction performed with few (sparse) projection views. That is, embodiments may be used for sparse image reconstruction, e.g., where each voxel is reconstructed from fewer than 100 detector signals, with or without MBIR. Use of SBP in such cases may reduce such aliasing/sampling effects by perturbing the backprojection process, thereby avoiding regular sampling patterns that are subject to aliasing. The technique is particularly useful to scenarios with mismatched voxel size and multi-resolution MBIR. Targeted, small-field-of-view MBIR in cone beam CT with minimal quality degradation is achievable through a multi-resolution, multi-field-of-view reconstruction.

Certain embodiments can be performed using a computer program or set of programs. The computer programs can exist in a variety of forms both active and inactive. For example, the computer programs can exist as software program(s) comprised of program instructions in source code, object code, executable code or other formats; firmware program(s), or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A method of computed tomography (CT) image reconstruction, the method comprising:
   acquiring, by a detector grid of a computed tomography system, detector signals for a location within an object of interest representing a voxel, wherein each detector signal of a plurality of the detector signals is obtained from an x-ray passing through the location at a different viewing angle;
   reconstructing a three-dimensional representation of at least the object of interest, the three-dimensional representation comprising the voxel, wherein the reconstructing comprises computationally perturbing a location of each detector signal of the plurality of detector signals within the detector grid, wherein the computationally perturbing corresponds to randomly perturbing a location of the x-ray within the voxel according to a uniformly distributed random number between 0 and a radius $R_s$ of a sphere contained by the voxel; and
   outputting the three-dimensional representation.

2. The method of claim 1, wherein the reconstructing comprises reconstructing according to a three-dimensional grid comprising the voxel and a plurality of other voxels, wherein each of the voxel and the plurality of other voxels has a same size.

3. The method of claim 1, wherein the reconstructing comprises reconstructing according to a three-dimensional grid comprising the voxel and a plurality of other voxels, wherein the voxel and the plurality of other voxels comprise voxels of at least two different sizes.

4. The method of claim 3, wherein the voxel and the plurality of other voxels consist of coarse voxels and fine voxels, wherein the object of interest is contained within the fine voxels.

5. The method of claim 1, wherein the acquiring, by the detector grid of the computed tomography system, the plurality of detector signals for the location within the object of interest consists of acquiring less than 100 detector signals.

6. The method of claim 1, wherein the outputting comprises displaying on a computer monitor.

7. The method of claim 1, wherein the randomly perturbing the location of the X-ray within the voxel comprises relocating to a distance from a center of the voxel, wherein the distance is obtained from a statistical random distribution.

8. The method of claim 1, wherein the randomly perturbing the location of the X-ray within the voxel comprises selecting a random direction from a center of the voxel.

9. The method of claim 1, further comprising modifying a Peters back-projection operator according to the computationally perturbing.

10. The method of claim 1, wherein the reconstructing comprises applying unmatched forward and back projections.

11. The method of claim 1, wherein each detector signal of the plurality of detector signals is obtained by directing an x-ray through the location at a different viewing angle.

12. The method of claim 1, wherein a perturbed ray position is computed according to $\hat{x}_\theta = U(0, R_s) \cdot s_\theta + x$, where $\hat{x}_\theta$ represents the perturbed ray position, $U(0, R_s)$ represents the uniformly distributed random number between 0 and the radius $R_s$ of the sphere contained by the voxel, $s_\theta$ represents a uniformly generated random vector describing a direction, and x represents an original position of a center of the voxel.

13. A system for computed tomography (CT) image reconstruction, the system comprising at least one electronic processor that executes instructions to perform operations comprising:
  acquiring, by a detector grid of a computed tomography system, detector signals for a location within an object of interest representing a voxel, wherein each detector signal of a plurality of the detector signals is obtained from an x-ray passing through the location at a different viewing angle;
  reconstructing a three-dimensional representation of at least the object of interest, the three-dimensional representation comprising the voxel, wherein the reconstructing comprises computationally perturbing a location of each detector signal of the plurality of detector signals within the detector grid, wherein the computationally perturbing corresponds to randomly perturbing a location of the x- ray within the voxel according to a uniformly distributed random number between 0 and a radius $R_s$ of a sphere contained by the voxel; and
  outputting the three-dimensional representation.

14. The system of claim 13, wherein the reconstructing comprises reconstructing according to a three-dimensional grid comprising the voxel and a plurality of other voxels, wherein each of the voxel and the plurality of other voxels has a same size.

15. The system of claim 13, wherein the reconstructing comprises reconstructing according to a three-dimensional grid comprising the voxel and a plurality of other voxels, wherein the voxel and the plurality of other voxels comprise voxels of at least two different sizes.

16. The system of claim 13, wherein the voxel and the plurality of other voxels consist of coarse voxels and fine voxels, wherein the object of interest is contained within the fine voxels.

17. The system of claim 13, wherein the acquiring, by the detector grid of the computed tomography system, the plurality of detector signals for the location within the object of interest consists of acquiring less than 100 detector signals.

18. The system of claim 13, wherein the outputting comprises displaying on a computer monitor.

19. The system of claim 13, wherein the randomly perturbing the location of the X-ray within the voxel comprises relocating to a distance from a center of the voxel, wherein the distance is obtained from a statistical random distribution.

20. The system of claim 13, wherein the randomly perturbing the location of the X-ray within the voxel comprises selecting a random direction from a center of the voxel.

21. The system of claim 13, wherein the operations further comprise modifying a Peters back-projection operator according to the computationally perturbing.

22. The system of claim 13, wherein the reconstructing comprises applying unmatched forward and back projections.

23. The system of claim 13, wherein each detector signal of the plurality of detector signals is obtained by directing an x-ray through the location at a different viewing angle.

24. The system of claim 13, wherein a perturbed ray position is computed according to $\hat{x}_\theta = U(0, R_s) \cdot s_\theta + x$, where $\hat{x}_\theta$ represents the perturbed ray position, $U(0, R_s)$ represents the uniformly distributed random number between 0 and the radius $R_s$ of the sphere contained by the voxel, $s_\theta$ represents a uniformly generated random vector describing a direction, and x represents an original position of a center of the voxel.

* * * * *